(12) United States Patent
Schiff et al.

(10) Patent No.: US 11,872,369 B1
(45) Date of Patent: Jan. 16, 2024

(54) WEARABLE MEDICAMENT DELIVERY DEVICE WITH LEAKAGE AND SKIN CONTACT SENSING AND METHOD OF USE THEREOF

(71) Applicant: Fresenius Kabi Deutschland GmbH, Bad Homburg (DE)

(72) Inventors: David R. Schiff, Highland Park, NJ (US); Vladlena Belozerova, Philadelphia, PA (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/178,799

(22) Filed: Feb. 18, 2021

(51) Int. Cl.
 *A61M 5/14* (2006.01)
 *A61M 5/142* (2006.01)
 *A61K 31/4015* (2006.01)
 *A61M 5/158* (2006.01)

(52) U.S. Cl.
 CPC ..... *A61M 5/14248* (2013.01); *A61K 31/4015* (2013.01); *A61M 2005/14252* (2013.01); *A61M 2005/1583* (2013.01); *A61M 2005/1585* (2013.01); *A61M 2205/15* (2013.01); *A61M 2205/3317* (2013.01); *A61M 2205/3584* (2013.01); *A61M 2205/50* (2013.01); *A61M 2205/8206* (2013.01)

(58) Field of Classification Search
 CPC .... A61M 5/14248; A61M 2005/14252; A61M 2005/1583; A61M 2005/1585; A61M 2205/15
 See application file for complete search history.

(56) References Cited

U.S. PATENT DOCUMENTS

| | | |
|---|---|---|
| 7,147,615 B2 | 12/2006 | Wariar et al. |
| 8,088,096 B2 | 1/2012 | Lauchard et al. |
| 9,061,097 B2 | 6/2015 | Holt et al. |
| 10,569,014 B2 | 2/2020 | Hanson et al. |
| 10,583,245 B2 | 3/2020 | McCullough et al. |
| 10,625,018 B2 | 4/2020 | Destefano et al. |

(Continued)

FOREIGN PATENT DOCUMENTS

| | | | |
|---|---|---|---|
| CN | 111249572 A * | 6/2020 | ........... A61B 5/0084 |
| EP | 2796157 B1 | 9/2016 | |

(Continued)

OTHER PUBLICATIONS

English translation of Chen (CN 111249572A).*

*Primary Examiner* — Courtney B Fredrickson
(74) *Attorney, Agent, or Firm* — Goodwin Procter LLP

(57) ABSTRACT

Described herein are wearable devices and methods for medicament delivery. Example devices can include a housing having an underside adapted to be proximate to a skin surface, and a reservoir disposed in the housing, the reservoir configured to be filled with a medicament to be delivered to the patient. The devices can include a cannula disposed within the housing and coupled to the reservoir, in which the cannula configured to protrude from a port defined by the housing to be positioned in the skin surface. The devices can further include a capacitive sensor configured to detect whether the medicament has leaked from the delivery device, in which the capacitive sensor includes a conductor disposed in a portion of the underside of the housing.

19 Claims, 6 Drawing Sheets

(56) References Cited

U.S. PATENT DOCUMENTS

| | | | |
|---|---|---|---|
| 10,646,664 B2 | 5/2020 | Lee et al. | |
| 10,682,474 B2 | 6/2020 | Ring et al. | |
| 10,758,683 B2 | 9/2020 | Gibson et al. | |
| 2002/0123740 A1* | 9/2002 | Flaherty | A61M 5/1452 604/890.1 |
| 2003/0009131 A1* | 1/2003 | Van Antwerp | A61M 5/16836 604/111 |
| 2009/0299267 A1* | 12/2009 | Durand | A61K 9/0009 604/20 |
| 2011/0105872 A1* | 5/2011 | Chickering, III | A61B 5/150297 600/365 |
| 2012/0010594 A1 | 1/2012 | Holt et al. | |
| 2014/0100522 A1* | 4/2014 | Nie | A61M 5/158 604/111 |
| 2015/0374919 A1 | 12/2015 | Gibson | |
| 2016/0038689 A1 | 2/2016 | Lee et al. | |
| 2016/0199574 A1 | 7/2016 | Ring et al. | |
| 2016/0296704 A1 | 10/2016 | Gibson | |
| 2016/0354555 A1 | 12/2016 | Gibson et al. | |
| 2017/0147787 A1 | 5/2017 | Albrecht et al. | |
| 2017/0182253 A1 | 6/2017 | Folk et al. | |
| 2017/0361015 A1 | 12/2017 | McCullough | |
| 2017/0368260 A1 | 12/2017 | McCullough et al. | |
| 2018/0001021 A1* | 1/2018 | Wu | A61M 1/3656 |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0256823 A1 | 9/2018 | Nazzaro et al. | |
| 2018/0304014 A1 | 10/2018 | Knudsen et al. | |
| 2019/0022306 A1 | 1/2019 | Gibson et al. | |
| 2019/0050375 A1 | 2/2019 | Fitzgibbon et al. | |
| 2019/0060562 A1 | 2/2019 | Olivas et al. | |
| 2019/0083702 A1 | 3/2019 | Nekouzadeh et al. | |
| 2019/0134296 A1 | 5/2019 | Barbedette et al. | |
| 2019/0143043 A1 | 5/2019 | Coles et al. | |
| 2019/0143047 A1 | 5/2019 | Jazayeri et al. | |
| 2019/0151544 A1 | 5/2019 | Stonecipher | |
| 2019/0167908 A1 | 6/2019 | Fitzgibbon et al. | |
| 2019/0192766 A1 | 6/2019 | Stonecipher | |
| 2019/0247579 A1 | 8/2019 | Damestani et al. | |
| 2019/0275241 A1 | 9/2019 | Ring et al. | |
| 2019/0328965 A1 | 10/2019 | Moberg | |
| 2019/0365986 A1 | 12/2019 | Coiner et al. | |
| 2019/0381238 A1 | 12/2019 | Stonecipher et al. | |
| 2020/0179609 A1 | 6/2020 | Tan-Malecki et al. | |
| 2020/0188585 A1* | 6/2020 | Petisce | A61M 5/16881 |
| 2020/0253525 A1* | 8/2020 | Zhang | A61B 5/0531 |

FOREIGN PATENT DOCUMENTS

| | | | |
|---|---|---|---|
| WO | WO-9924145 A1 * | 5/1999 | A61M 1/3656 |
| WO | 2014143770 A1 | 9/2014 | |
| WO | 2015187797 A1 | 12/2015 | |
| WO | 2016100055 A1 | 6/2016 | |
| WO | 2016130679 A2 | 8/2016 | |
| WO | 2016133947 A1 | 8/2016 | |
| WO | 2016145094 A2 | 9/2016 | |
| WO | 2016130679 A3 | 11/2016 | |
| WO | 2017120178 A1 | 7/2017 | |
| WO | 2017200989 A1 | 11/2017 | |
| WO | 2018081234 A1 | 5/2018 | |
| WO | 2018151890 A1 | 8/2018 | |
| WO | 2018164829 A1 | 9/2018 | |
| WO | 2018165499 A1 | 9/2018 | |
| WO | 2018183039 A1 | 10/2018 | |
| WO | 2018226515 A1 | 12/2018 | |
| WO | 2018226565 A1 | 12/2018 | |
| WO | 2018236619 A1 | 12/2018 | |
| WO | 2018237225 A1 | 12/2018 | |
| WO | 2019014014 A1 | 1/2019 | |
| WO | 2019018169 A1 | 1/2019 | |
| WO | 2019022950 A1 | 1/2019 | |
| WO | 2019022951 A1 | 1/2019 | |
| WO | 201932101 A1 | 2/2019 | |
| WO | 2019032482 A2 | 2/2019 | |
| WO | 2019070472 A1 | 4/2019 | |
| WO | 2019070552 A1 | 4/2019 | |
| WO | 2019074579 A1 | 4/2019 | |
| WO | 2019089178 A1 | 5/2019 | |
| WO | 2019090303 A1 | 5/2019 | |
| WO | 2019143753 A1 | 7/2019 | |

* cited by examiner

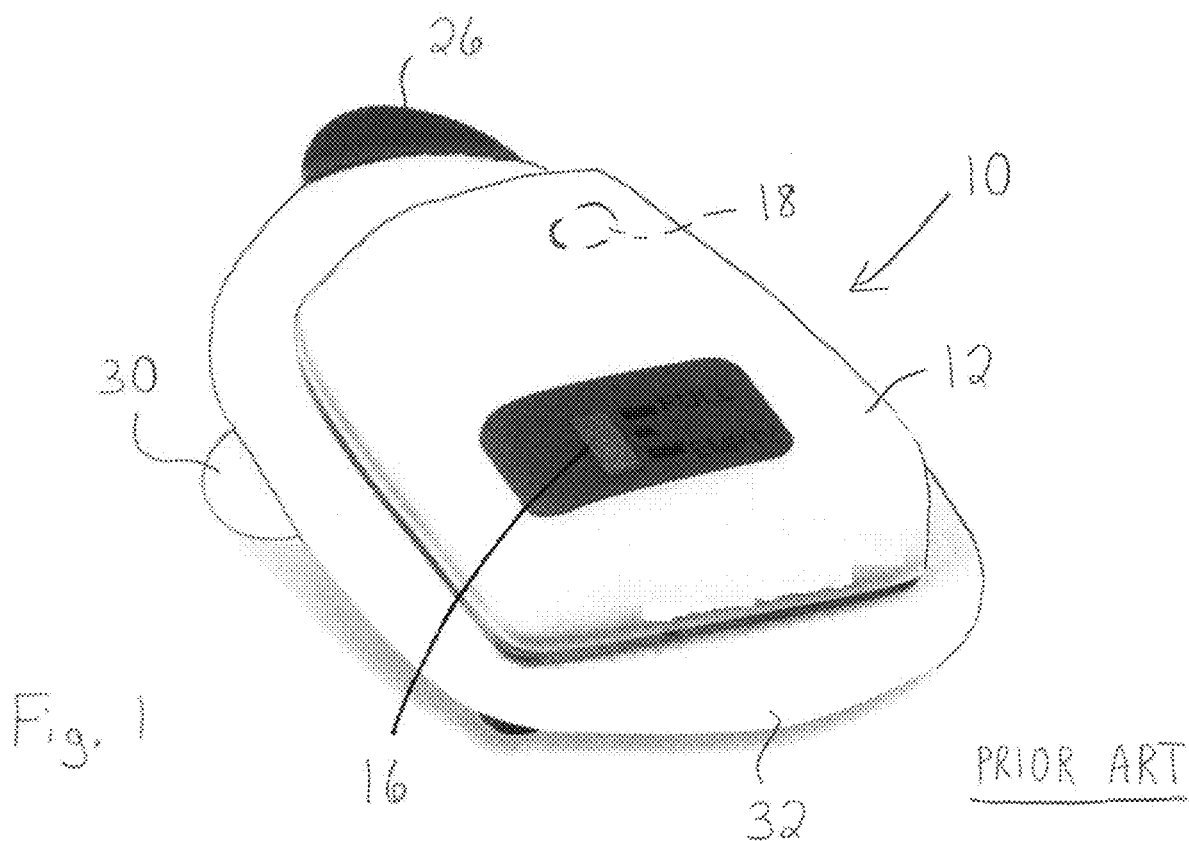
Fig. 1 PRIOR ART
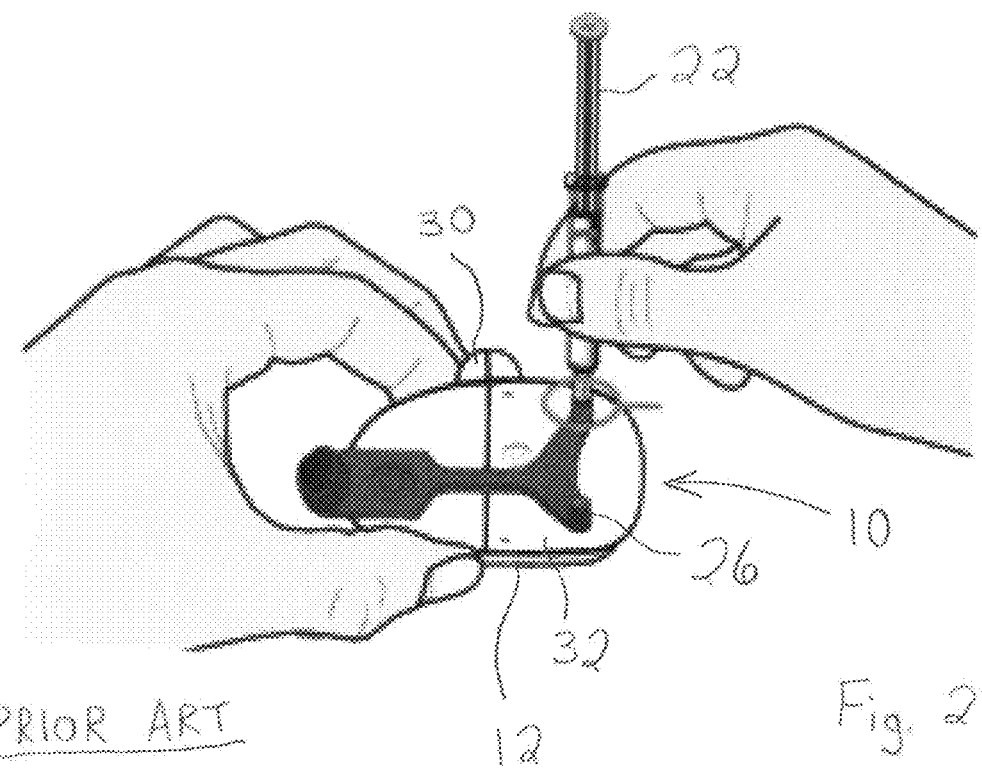
PRIOR ART Fig. 2

WEARABLE MEDICAMENT DELIVERY DEVICE WITH LEAKAGE AND SKIN CONTACT SENSING AND METHOD OF USE THEREOF

TECHNICAL FIELD

The present disclosure generally relates to drug delivery devices and, more particularly, a drug delivery device capable of being worn by a patient while the drug delivery device delivers a drug to the patient.

BACKGROUND

Delivery of medicaments, e.g., liquid drugs, to a patient via injection using a needle or syringe is well-known. More recently, devices that automate the delivery of medicaments have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the medicament into the body of the patient at one or more scheduled times. For example, a device may be configured to deliver a medicament over the span of 45 minutes, with delivery beginning 27 hours after the device has been activated and applied to a patient (to ensure that the medicament is not delivered sooner than 24 hours after a medical procedure or treatment). These devices improve upon manual methods by obviating the need for the patient to inject themselves with the medicament (which carries heightened risks of the patient improperly administering the injection or injecting the medicament at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a medicament to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the medicament to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a medicament delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. A battery 20 provides power to the status light 18 and the other electrical components of the device 10.

The medicament is injected into the reservoir 14 using a (typically pre-filled) syringe 22 via a port 24 incorporated into the bottom or underside of the housing 12 (FIG. 4) and fluidly connected to the reservoir 14. FIGS. 1 and 2 illustrate an applicator 26 that is removably associated with the underside of the housing 12 and used in combination with the syringe 22 to fill the reservoir 14 via the port 24. The medicament is most typically injected into the reservoir 14 by a medical professional immediately before the device 10 is secured to the patient to ensure that the proper medicament is supplied, along with the proper amount.

A piston or plunger 28 (FIG. 4) positioned within the reservoir 14 is moved (from left to right, in the orientation of FIG. 4) as the space within the reservoir 14 is filled by the inflowing medicament. Movement of the piston 28 into its final position (when the reservoir 14 has been filled with the appropriate amount of the medicament) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the medicament out of the reservoir 14 (e.g., 27 hours after the device 10 has been activated) will cause the medicament to move into the needle 38 (via the proximal end of the needle 38), through the needle 38 (to its distal end), and into the cannula 34. The medicament is then delivered to the patient (e.g., over the course of a 45-minute session) via the distal end of the cannula 34 positioned within the skin.

As for the mechanism by which the medicament is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 allow the lever 54 to stay electrically coupled to the electrical contacts 76 and 82 (which are electrically coupled to the above-referenced printed circuit board) as the lever 54 pivots about the pivot point 56.

At the designated time (e.g., 27 hours after the device 10 has been activated), the controller provides commands that cause the lever 54 to be alternately pivoted about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are contained within a single part and are associated with a common shaft 84 (FIG. 3), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the medicament out of the reservoir 14 via the proximal end of the needle 38. As described above, the medicament will flow through the needle 38, into and through the cannula 34, and into the body of the patient.

After the medicament has been delivered (e.g., over the course of a 45-minute session), the controller alerts the patient via a visual cue from the status light 18 and/or an audible cue from the buzzer that medicament delivery is complete. Subsequently, the patient removes the device 10 from their skin and discards the device 10.

While devices of the type described above have proven adequate, there is room for improvement of them. For example, there is a need for on-person or wearable medicament delivery devices that provide more efficient and reliable medicament pumping mechanisms. There is also a need for medicament delivery devices that are smaller in size, lower profile, less likely to be caught on clothing or become dislodged, and/or more comfortable to wear.

SUMMARY

In general, in one aspect, the subject matter of this disclosure relates to a medicament delivery device including a housing having an underside adapted to be proximate to a skin surface, and a reservoir disposed in the housing. The reservoir can be configured to be filled with a medicament to be delivered to the patient. The medicament delivery device can include a cannula disposed within the housing and coupled to the reservoir. The cannula can be configured to protrude from a port defined by the housing to be positioned in the skin surface. The medicament delivery device can include a capacitive sensor configured to detect whether the medicament has leaked from the delivery device. The capacitive sensor can include a conductor disposed in a portion of the underside of the housing.

Various embodiments of the medicament delivery device can include one or more of the following features. The conductor can be a printed trace on a flexible circuit. The flexible circuit can be integrated in or coupled to the housing. The capacitive sensor can include a circuit configured to determine a change in capacitance due to leakage of the medicament. The capacitive sensor can include a communication device configured to wirelessly transmit a signal indicating whether the medicament has leaked from the delivery device.

The communication device can be a Bluetooth® device configured to be paired with a Bluetooth® device of a mobile device. The circuit can be configured to differentiate the change in capacitance due to the leakage of the medicament from another change in capacitance due to a bodily fluid. The medicament can include pegfilgrastim. The portion of the underside of the housing can be an area proximate an outer perimeter of the housing. The portion of the underside of the housing can be an area proximate the port.

The device can include an adhesive pad coupled to the underside of the housing and configured to adhere the housing to the skin surface, in which the conductor is disposed adjacent to the adhesive pad. The device can include a battery configured to power the capacitive sensor. The device can include a material coupled to the housing and configured to change colors when the medicament has leaked from the delivery device. The material can be part of or integrated into an adhesive pad coupled to the underside of the housing, in which the adhesive pad is configured to adhere the housing to the skin surface.

The cannula can be adapted to (i) fluidically connect with the reservoir, (ii) pass through the port defined in the housing into the skin surface, and (iii) deliver the medicament to the patient. The device can include a needle, in which, when piercing the skin surface, the needle is configured to move the cannula such that the cannula is positioned in the skin surface, and after the cannula is positioned in the skin surface, the needle is configured to retract from the skin surface. The device can include a spring mechanism configured to move the needle along a track such that (i) the needle pierces the skin surface, and (ii) the needle retracts from the skin surface.

The device can include a controller coupled to at least one of: the reservoir or the cannula and configured to execute a delivery of the medicament to the patient. The device can include a status indicator coupled to the controller and configured to indicate at least one of: (a) that the device is ready to be applied to the patient; (b) that the device is operating properly; or (c) that the device is experiencing an error state.

In another aspect, the subject matter of this disclosure relates to a method for detecting a leak from a medicament delivery device. The method can include providing a medicament delivery device including a housing having an underside adapted to be proximate to a skin surface, and a reservoir disposed in the housing. The reservoir can be configured to be filled with a medicament to be delivered to the patient. The device can include a cannula disposed within the housing and coupled to the reservoir, in which the cannula is configured to protrude from a port defined in the housing to pierce the skin surface, and a capacitive sensor configured to detect whether the medicament has leaked from the reservoir or the cannula, in which the capacitive sensor can include a conductor disposed in a portion of the underside of the housing. The method can include delivering, by the delivery device, the medicament to the patient and detecting, by the capacitive sensor, whether the medicament has leaked from the delivery device.

In certain examples, the method can include transmitting, by the capacitive sensor, a signal indicating that the medicament has leaked from the delivery device.

In another aspect, the subject matter of this disclosure relates to a medicament delivery device. The medicament delivery device can include a housing having an underside adapted to be proximate to a skin surface, and a reservoir disposed in the housing, the reservoir configured to be filled with a medicament to be delivered to the patient. The device can include a cannula disposed within the housing and coupled to the reservoir, in which the cannula is configured to protrude from a port defined by the housing to be positioned in the skin surface, and a material coupled to the housing and configured to change colors when the medicament has leaked from the delivery device.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1 is a schematic, perspective view of a known drug delivery device.

FIG. 2 is a schematic, bottom view of the device of FIG. 1 being filled with a drug.

DETAILED DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art and are considered to be within the scope of the disclosed invention.

It should be understood that the order of steps or order for performing certain actions is immaterial, so long as the invention remains operable. Moreover, two or more steps or actions may be conducted simultaneously.

As used herein, the term "medicament" and "drug" may be used interchangeably and can include any medication, medicine, drug, pharmaceutical, biologic, placebo, etc. in liquid, gel, powder, or gas form. In some embodiments, two or more medicaments may be included in the delivery device. The two or more medicaments may be delivered at separately or combined for delivery to the patient wearing the delivery device.

Wearable Delivery Device Leakage

Figure 3:
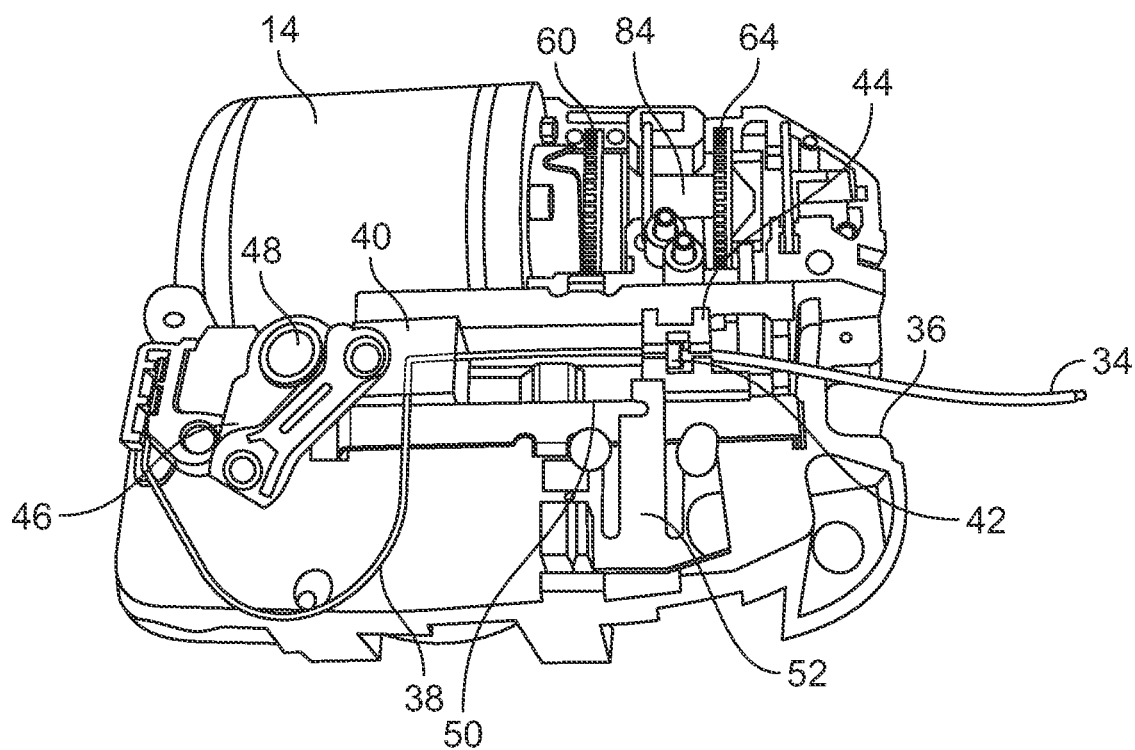
FIGS. 3 and 4 are images of functional components of the device of FIG. 1 in which an exterior housing of the device has been removed.
Figure 4:
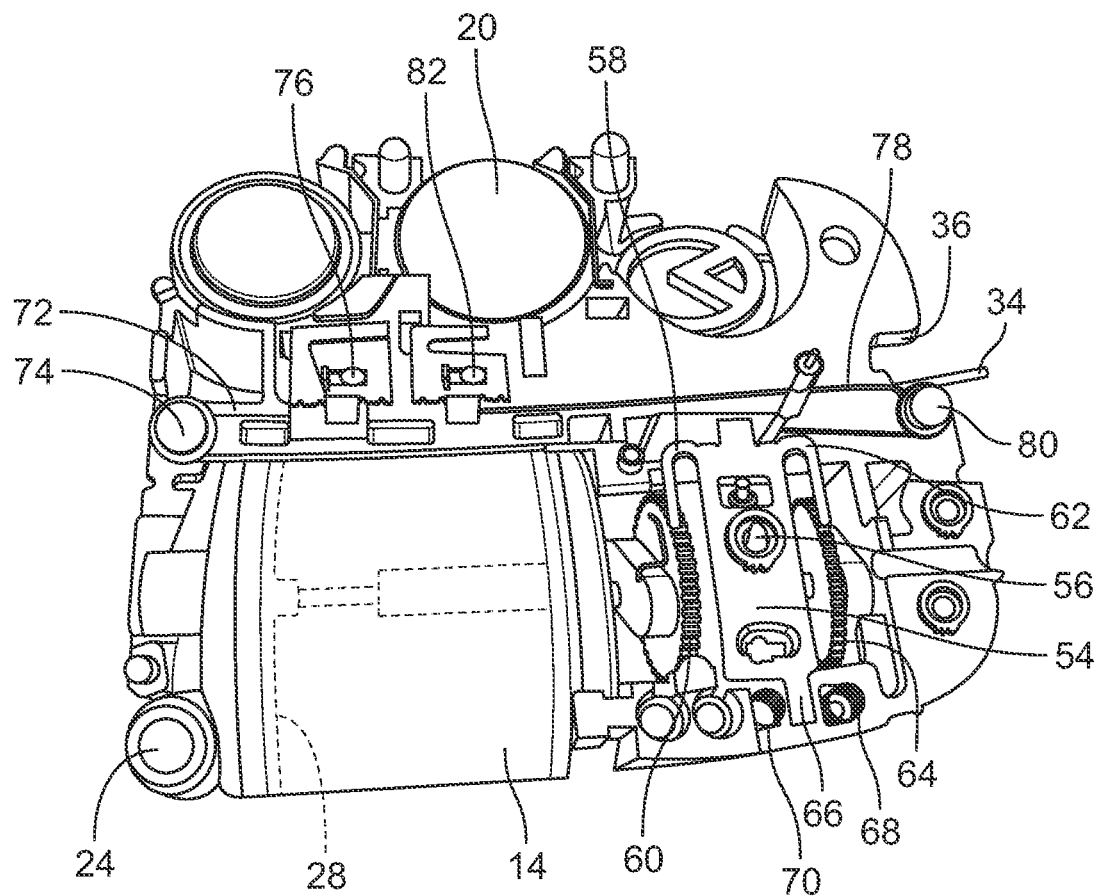
Figure 5A:
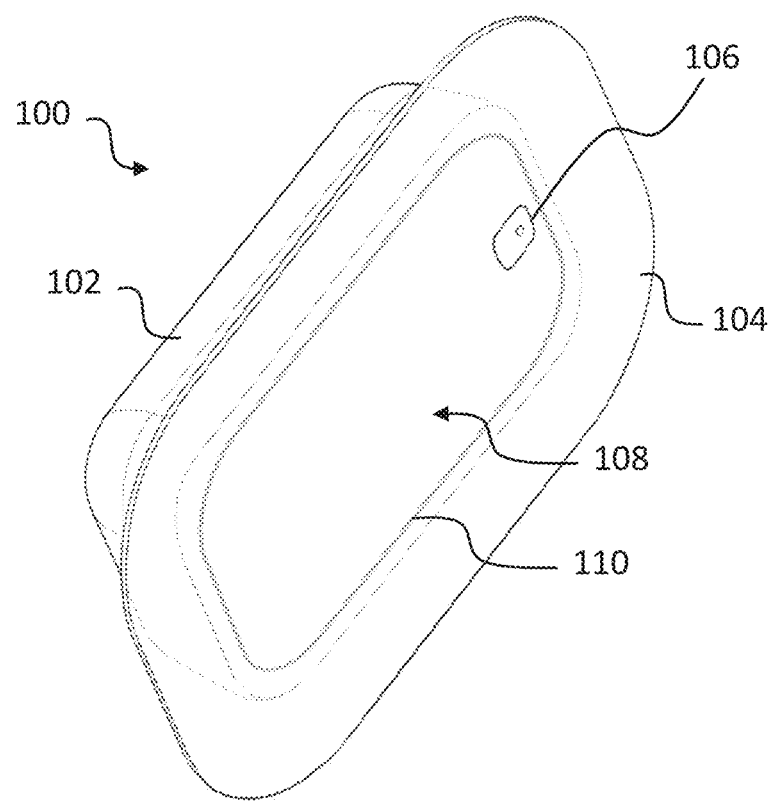
FIG. 5A is a schematic, perspective view of a medicament delivery device having a capacitive sensor configured to detect leaks from the device, in accordance with certain embodiments of the invention.
Figure 5B:
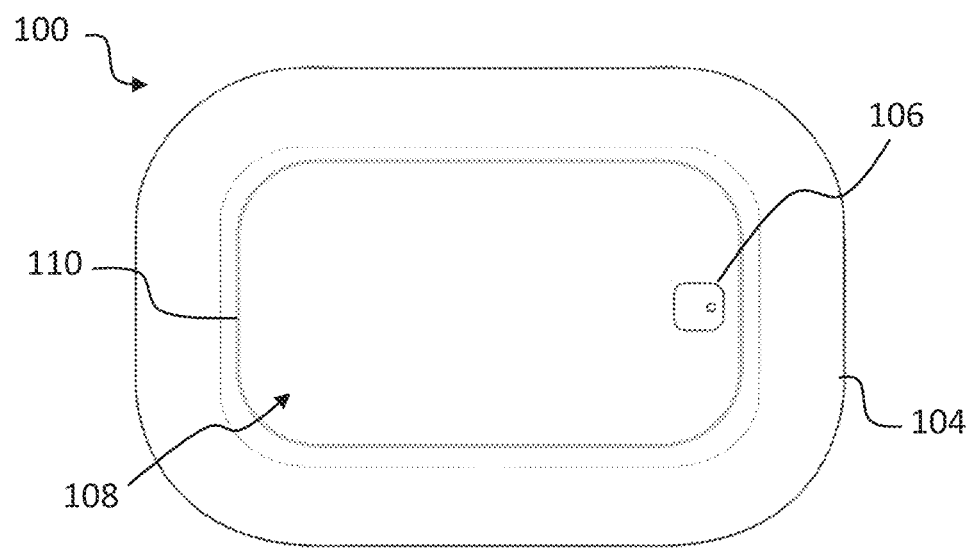
FIG. 5B is a schematic, bottom view of the medicament delivery device of FIG. 5A.

FIGS. 5A and 5B illustrate an exemplary embodiment of a wearable delivery device 00 including a housing 102 and an adhesive pad 104. The housing 102 can be attached to the adhesive pad 104, which is used to secure the device 100 to a skin surface of the patient. The housing 102 can include a reservoir 14 configured to hold a medicament. A cannula 34 connected to the reservoir 14 can be configured to deliver the medicament from the reservoir 14 through the port 106. At a point during which the delivery device 100 is mounted (e.g., adhered via the adhesive pad 104) to a patient, the cannula 34 is configured to deliver the medicament through the skin surface of the patient. In some implementations, the adhesive pad 104 may extend over most of the underside 108 of the housing 102. For example, the adhesive pad may be configured such that only the port 106 is exposed to the skin surface (to allow for medicament delivery via the cannula). In some implementations, the adhesive pad 104 may be attached to a perimeter of the underside 108 of the housing 102, exposing a larger portion of the underside 108, including the port 106, to the patient's skin.

In various embodiments, the wearable delivery device 100 can be configured to detect a leak from the delivery device 100. For instance, the leak may originate from one or more portions of the device 100, e.g., the reservoir 14, the cannula 34, and/or the port 106. A leak from the delivery device 100 can be detrimental to the operation of the wearable delivery device 100 and/or to the health of the patient. For instance, even a small leak from the reservoir or cannula inside the device 100 can harm an electronic circuit (e.g., controller or processor configured to execute a medicament delivery routine) inside the device 100. For example, a leak of a liquid medicament can cause a short circuit or cause the circuit to operate improperly (e.g., execute a delivery routine at incorrect times and/or in incorrect doses).

In some cases, a leak outside the housing 102 or adhesive pad 104 can reduce the adherence of the pad 104 to the skin surface, thereby causing the wearable device 100 to detach from the skin surface. Detachment of the device 100 may not only render the device useless to the patient but may also harm the patient if the cannula and/or needle is embedded in the patient's skin at the time of detachment. In another example, the leaked medicament may be (i) intended to be mixed with another medicament, (ii) intended to be stored or delivered at a particular temperature, and/or (iii) safe for internal use but not for external use. In such instances, the leaked medicament itself may harm the skin surface of the patient (e.g., by adverse chemical reaction or causing a rash or other skin irritant). In another example, the leaked medicament may adversely interact with a material of the adhesive pad 104 and/or housing 102 and cause harm to the patient's skin.

In some cases, the leakage from the device and/or a leakage at the injection site may adversely affect patient treatment and/or health outcome. For instance, if the timing, dose, therapy duration, frequency, etc. is critical to the treatment, a leak may affect the efficacy of the device 100 such that the device is not able to deliver the medicament at the intended time, with the intended dose, for the intended duration, at the intended frequency, etc. For example, if the patient does not receive the intended dose of the medicament, the therapy may not succeed, thereby adversely affecting the patient's health.

In some instances, the patient may not be aware of the leakage until it is too late (e.g., the device malfunctions or patient is harmed by the leak). Accordingly, detecting a leak from the device can be beneficial to the proper and effective operation of the wearable delivery device.

Capacitive Sensors for Wearable Delivery Devices

In some implementations, a wearable delivery device 100 may include or be coupled to a sensor (e.g., a capacitive sensor) configured to detect leakage from the device 100. In general, this application will often describe capacitive sensors, but in other embodiments, other suitable types of sensors can also be used. A capacitive sensor may include one or more conductors or electrodes attached to a portion of device 100. Referring to FIGS. 5A and 5B, the conductor 110 may be attached to bottom surface of the adhesive pad 104 and/or to the housing underside 108. The conductor 110 may be a wire or trace made of a metal or metal alloy, e.g., copper, aluminum, gold, silver, steel, brass, zinc, nickel, etc. As described further below, the conductor 110 may be arranged in one or more loop shapes or other shapes conducive to leakage detection. For example, the conductor 110 may be arranged in other closed or nearly closed shapes (e.g., square, rectangular, polygonal, circular, elliptical, symmetrical, asymmetrical, etc.). The shape of conductor 110 may follow the perimeter of the needle port 106. As depicted in FIGS. 5A-5B, the conductor 110 may be arranged proximate the perimeter of the housing underside 108 and/or follow the general shape of the adhesive pad 104. In some implementations, the shape of the conductor 110 may be such that the capacitive sensor can detect leaks from the reservoir and/or the housing 102. For example, housing 102 may be formed from two or more pieces of plastic or other material that come together at one or more seams. Accordingly, the conductor 110 may be positioned proximate to and/or shaped to follow a seam of the housing 102.

Figure 6A:
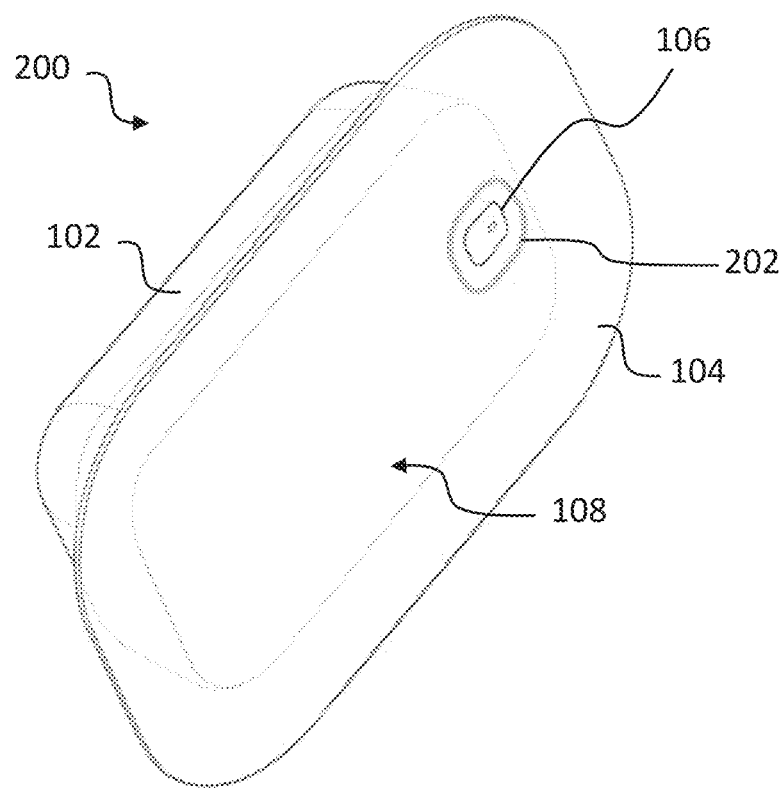
FIG. 6A is a schematic, perspective view of a medicament delivery device having a capacitive sensor configured to detect leaks from the device, in accordance with certain embodiments of the invention.
Figure 6B:
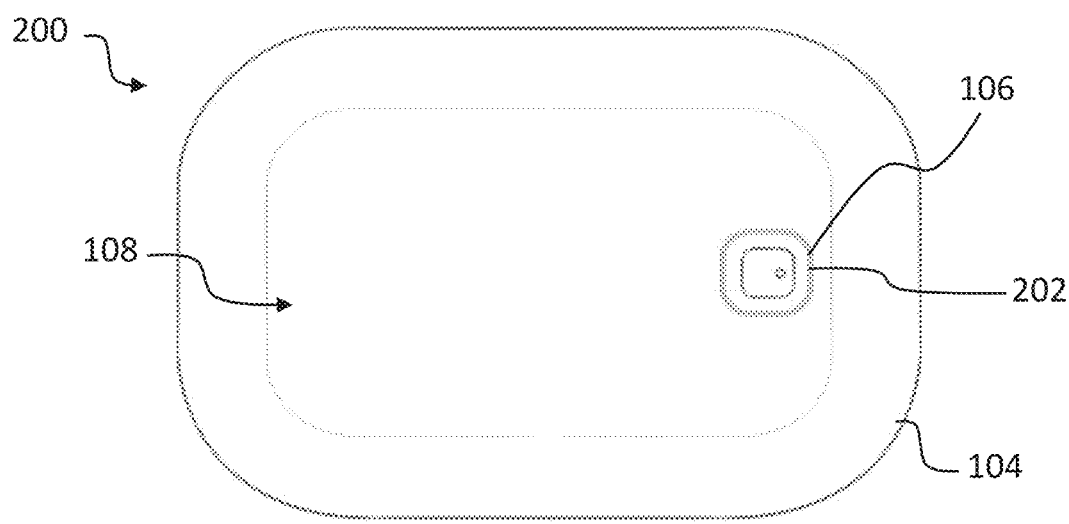
FIG. 6B is a schematic, bottom view of the medicament delivery device of FIG. 6A.

FIGS. 6A-6B illustrate another example embodiment of the wearable delivery device 200, which includes device components (e.g., housing 102, adhesive pad 104, port 106, housing underside 108) as described for the device 100. The device 200 can include a capacitive sensor having a conductor 202 arranged proximate the port 106 (e.g., surrounding all or a portion of the perimeter of the port 106). The shape of the conductor 202 may be such that the capacitive sensor can detect leaks near or from the port 106 (e.g., from the needle, cannula, or port 106 itself). In some implementations, the shape of conductor 202 may follow the general shape of the port 106.

Figure 7:
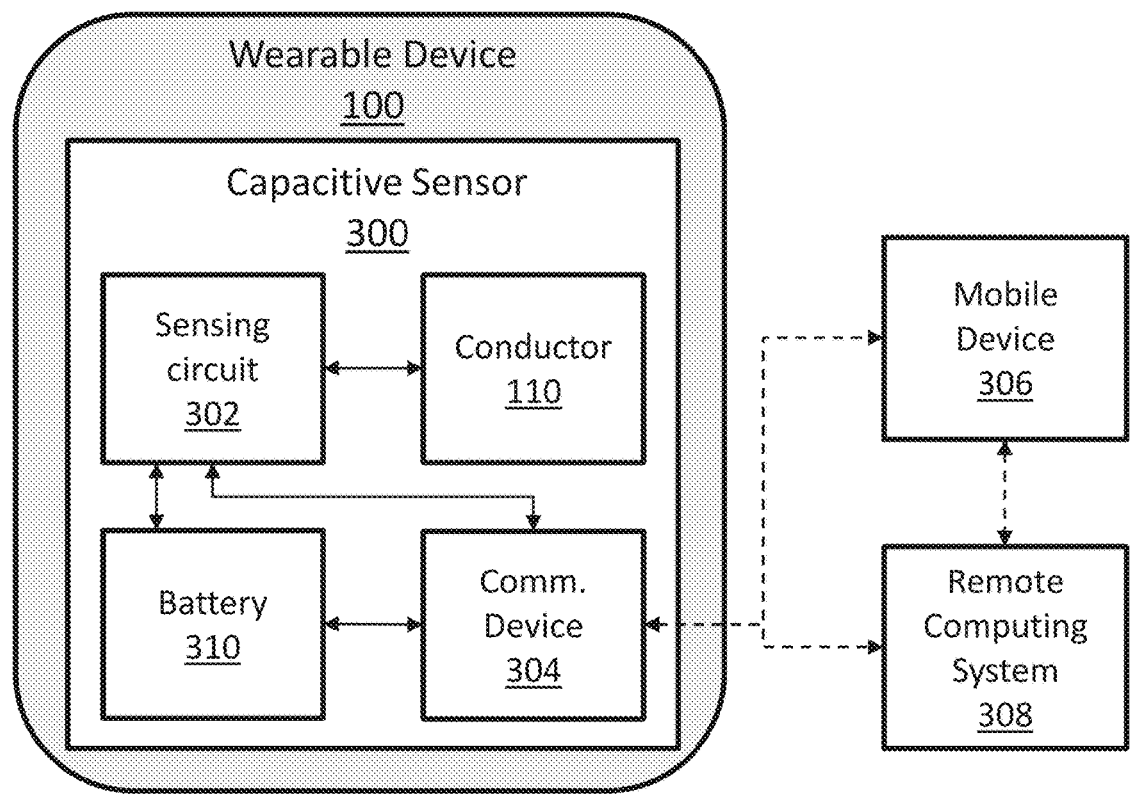
FIG. 7 is a diagram of a capacitive sensor for a medicament delivery device, in accordance with certain embodiments of the invention.

FIG. 7 illustrates an example capacitive sensor 300 for a wearable delivery device (e.g., device 100 or 200). The capacitive sensor 300 may include one or more conductors (e.g., conductor 110 or 202) coupled to a sensing circuit 302. The conductor(s) may be a shaped wire or a printed trace on a circuit board (e.g., a flexible circuit board). In some implementations, the conductor(s) 110 may be integrated into housing underside 108 or adhesive pad 104. For example, the conductive trace 110 may be printed directly on the outer surface of the housing underside 108. In another example, the conductive trace 110 may be woven into the material of adhesive pad 104.

In some implementations, the sensing circuit 302 may feed a current to the conductor 110 such that the conductor 110 generates an electromagnetic field. For example, the conductor 110 may be arranged in one or more loop shapes to generate the electromagnetic field. Upon contacting the conductor 110, a liquid can change the capacitance of the conductor 110. The change in capacitance can be sensed by a processor in the circuit 302. For example, when the housing underside 108, the adhesive pad 104, and/or the skin surface adjacent to the conductor (e.g., 110 or 202) is wetted (e.g., by a liquid medicament), the difference in capacitance can be detected by the sensing circuit 302. In some implementations, the capacitive sensor 300 can be configured to detect the change in capacitance due to a medicament leakage instead of bodily fluid (e.g., sweat or blood). In some embodiments, the conductor (e.g., conductor 110 or 202) may be disposed on or in a pad on the underside of the housing 108. The pad (also referred to as a wicking pad) may absorb or wick fluid such that the conductor can better distinguish the particular difference in capacitance due to medicament leakage as compared to other fluids. The wicking pad may be part of or separate from the adhesive pad 104. In some embodiments, a first conductor may be positioned in a part of the pad that is expected to stay dry during a leakage (e.g., a part of the pad closest to the housing underside or at the very edges of the pad) and a second conductor may be positioned in a part of the pad that is expected to become wet during a leakage. The relative capacitance measurements in the first conductor as compared to the second conductor may be used to provide a more accurate determination of the type of fluid.

In some implementations, the capacitive sensor 300 can include a communication device 304 coupled to the sensing circuit 302. The communication device 304 can be configured to receive a signal from the sensing circuit 302 indicating that a leak was detected by the sensing circuit. The communication device 304 can include a transmitter configured to wirelessly transmit a signal indicative of the leakage to a mobile device 306 or a remote computing system 308. For example, the communication device 304 may communicate via a Bluetooth® device (e.g., Bluetooth® Low Energy (BLE) device), a Wi-Fi module, near-field communication (NFC) device, a radio device, a cellular unit, etc. The mobile device 306 may be a standalone electronic device, a smartphone, a smartwatch, a tablet, a laptop computer, a notebook computer, a headset, a headphone, etc. The remote computing system 308 may be a server system configured to store (e.g., in memory) and/or communicate patient information to a healthcare provider (e.g., a primary care provider at a doctor's office, a clinician, a medical professional at a hospital, etc.) via a web and/or intranet portal.

In some implementations, the communication device 304 may include a Bluetooth® device paired with the Bluetooth® device of a patient's mobile device 306 (e.g., smartphone). Upon detecting a leakage in the patient's wearable delivery device 100, the communication device 304 may send a signal indicating the leakage to a mobile device 306. The device 306 may send a message over the Internet via a Wi-Fi connection to a remote computer system 308. In some implementations, the mobile device 306 may have an application configured to present information related to the wearable delivery device (e.g., 100 or 200) via a user interface. The application may be configured to notify the patient of the leakage in the wearable device. The patient may then be able to mitigate the leak, remove the wearable device, and/or contact a healthcare provider. In some embodiments, the capacitive sensor 300 (e.g., via the sensing circuit 302 or communication device 304) may send a signal indicative of the leakage to a processor of the wearable delivery device 100. In such a case, the processor may send a signal to change a color, brightness, or flashing of the status light of the device housing 102. The capacitive sensor 300 may include one or more batteries 310 configured to power the sensing circuit 302 and/or communication device 304. In some implementations, a battery of the wearable delivery device 100 itself (e.g., outside of or separate from the capacitive sensor 300) can power the capacitive sensor 300.

Example low, high, and typical values for parameters related to embodiments of the wearable delivery device (e.g., 100 or 200) having a capacitive sensor 300 are provided in Table 1. The listed values can be minimum, maximum, or average dimensions. Various embodiments include any parameter value (e.g., integer or decimal value) within the cited ranges. Express support and written description of these values for each parameter are hereby represented. For example, the length L of the conductor 110 can be 15, 16, 17, . . . , 74, or 75 mm.

TABLE 1

Exemplary parameters of a wearable delivery device having a capacitive sensor.

| Parameter | Low | Typical | High |
| --- | --- | --- | --- |
| Conductor 110 | | | |
| Conductor length L (mm) | 15 | 35 | 75 |
| Conductor width W (mm) | 3 | 20 | 60 |
| Conductor thickness (mm) | 0.1 | 0.3 | 1 |
| Conductor 202 | | | |
| Conductor length L (mm) | 3 | 5 | 10 |
| Conductor width W (mm) | 1 | 3 | 5 |
| Conductor thickness (mm) | 0.1 | 0.3 | 1 |
| Other | | | |
| Current (mA) | 1 | 100 | 1500 |
| Operating distance (mm) | 0 | 10 | 30 |
| Operating frequency (Hz) | 1 | 10 | 25 |
| Operating temperature (° C.) | −25 | 33 | 70 |

Methods for Leak Detection in Wearable Delivery Devices

Figure 8:
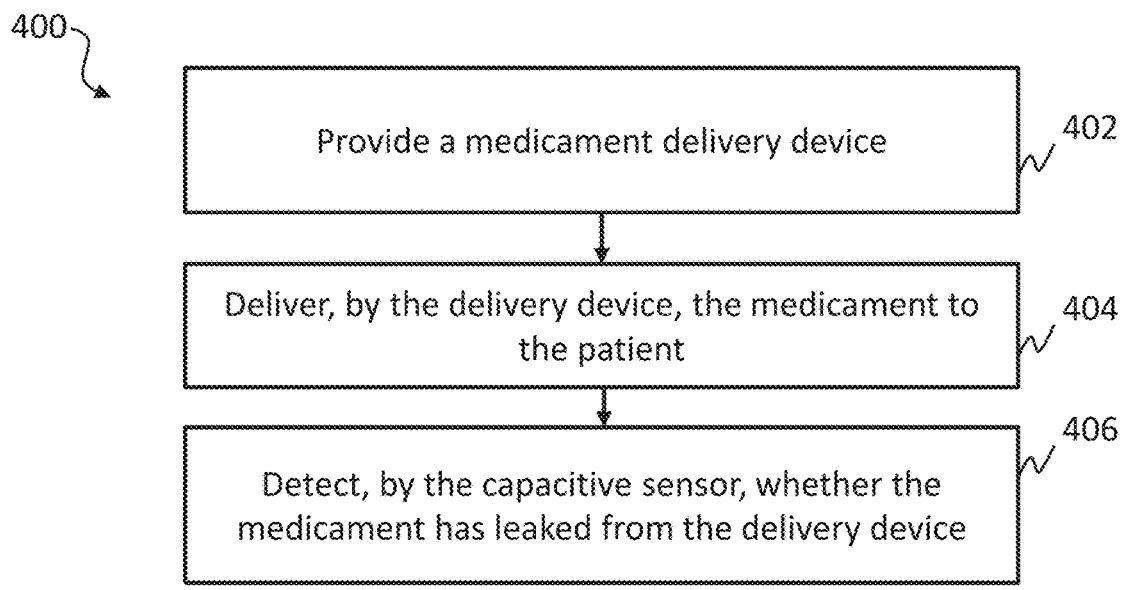
FIG. 8 is a flowchart of a method of delivering a medicament, in accordance with certain embodiments of the invention.

FIG. 8 is a flowchart of an example method 400 of delivering a drug. In step 402, a medicament delivery device is provided. The medicament delivery device can be device 100, device 200, or a variant thereof. In step 404, the delivery device can deliver the medicament to the patient (e.g., by the example techniques described herein). In step 406, the sensing circuit 302 coupled to the conductor 110 of sensor 300 can detect whether the medicament has leaked from the delivery device 100. In some implementations, a communication device 304 of the capacitive sensor 300 can be configured to receive a signal from the sensing circuit 302 indicative of a leakage. The communication device 304 may transmit a signal to another device (e.g., mobile device 306 or remote computing system 308) indicating that the medicament has leaked from the device 100.

Materials for Leakage Detection

In some implementations, a wearable delivery device (e.g., 100 or 200) may include or be attached to a material configured to change one or more properties upon a leakage from the wearable delivery device. For example, the material may be configured to change colors, temperature, texture, etc. so as to indicate to the patient or healthcare provider that a leak has occurred. In some implementations, the material may be configured to distinguish between leakage from the device and a bodily fluid (e.g., blood, sweat, etc.). In some implementations, the material can be configured based on the medicament to be delivered by the device. For example, the material may change properties (e.g., color) based on the chemical composition of the medicament. In some implementations, a non-toxic or inactive chemical can be added to the medicament that may interact with the material and cause the material to change properties (e.g., color). The material may be a wicking or absorptive pad configured to change color when wetted with a fluid. The material may be applied to the underside 108 of the device. In some embodiments, the material may be integrated or applied to the adhesive pad 104.

While the specification describes methods and devices for filling injector devices with pegfilgrastim, the teachings herein may be used to implement methods for filling injector devices and syringes containing other liquids, such as solutions, which may comprise any of adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention.

The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A medicament delivery device comprising:
   a housing having an underside comprising an adhesive pad adapted to be proximate to a skin surface;
   a reservoir disposed in the housing, the reservoir configured to be filled with a medicament to be delivered to a patient;
   a cannula disposed within the housing and coupled to the reservoir, the cannula configured to protrude from a port defined by the housing to be positioned in the skin surface; and
   a capacitive sensor configured to detect whether the medicament has leaked from the delivery device, the capacitive sensor comprising a first conductor surrounding the port and disposed in a portion of the underside of the housing and a second conductor disposed in the adhesive pad and at an edge thereof in a position that is expected to stay dry during a leakage.

2. The device of claim 1, wherein the first conductor is a printed trace on a flexible circuit, the flexible circuit integrated in or coupled to the housing.

3. The device of claim 1, wherein the capacitive sensor comprises a circuit configured to determine a change in capacitance due to leakage of the medicament.

4. The device of claim 3, wherein the capacitive sensor comprises a communication device configured to wirelessly transmit a signal indicating whether the medicament has leaked from the delivery device.

5. The device of claim 3, wherein the medicament comprises pegfilgrastim.

6. The device of claim 1, wherein the portion of the underside of the housing is an area proximate an outer perimeter of the housing.

7. The device of claim 1, wherein the portion of the underside of the housing is an area proximate the port.

8. The device of claim 1, wherein the adhesive pad is configured to adhere the housing to the skin surface.

9. The device of claim 1, further comprising:
   a battery configured to power the capacitive sensor.

10. The device of claim 1, further comprising:
    a material coupled to the housing and configured to change colors when the medicament has leaked from the delivery device.

11. The device of claim 10, wherein the material is part of or integrated into the adhesive pad coupled to the underside of the housing, the adhesive pad configured to adhere the housing to the skin surface.

12. The device of claim 1, wherein the cannula is adapted to (i) fluidically connect with the reservoir, (ii) pass through the port defined in the housing into the skin surface, and (iii) deliver the medicament to the patient.

13. The device of claim 12, further comprising a needle, wherein:
    when piercing the skin surface, the needle is configured to move the cannula such that the cannula is positioned in the skin surface, and
    after the cannula is positioned in the skin surface, the needle is configured to retract from the skin surface.

14. The device of claim 13, further comprising:
    a spring mechanism configured to move the needle along a track such that:
    (i) the needle pierces the skin surface, and
    (ii) the needle retracts from the skin surface.

15. The device of claim 1, further comprising:
    a controller coupled to at least one of: the reservoir or the cannula and configured to execute a delivery of the medicament to the patient.

16. The device of claim 15, further comprising:
    a status indicator coupled to the controller and configured to indicate at least one of:
    (a) that the device is ready to be applied to the patient;
    (b) that the device is operating properly; or
    (c) that the device is experiencing an error state.

17. A method for detecting a leak from a medicament delivery device, the method comprising:
    providing a medicament delivery device comprising:
      a housing having an underside comprising an adhesive pad adapted to be proximate to a skin surface;
      a reservoir disposed in the housing, the reservoir configured to be filled with a medicament to be delivered to a patient;

a cannula disposed within the housing and coupled to the reservoir, the cannula configured to protrude from a port defined in the housing to pierce the skin surface; and a capacitive sensor configured to detect whether the medicament has leaked from the reservoir or the cannula, the capacitive sensor comprising a first conductor surrounding the port and disposed in a portion of the underside of the housing and a second conductor disposed in the adhesive pad and at an edge thereof in a position that is expected to stay dry during a leakage;

delivering, by the delivery device, the medicament to the patient; and detecting, by the capacitive sensor, whether the medicament has leaked from the delivery device.

18. The method of claim 17, further comprising:

transmitting, by the capacitive sensor, a signal indicating that the medicament has leaked from the delivery device.

19. A medicament delivery device comprising:

a housing having an underside comprising an adhesive pad adapted to be proximate to a skin surface;

a reservoir disposed in the housing, the reservoir configured to be filled with a medicament to be delivered to a patient;

a cannula disposed within the housing and coupled to the reservoir, the cannula configured to protrude from a port defined by the housing to be positioned in the skin surface, a capacitive sensor comprising a first conductor surrounding the port and disposed in a portion of the underside of the housing and a second conductor disposed in the adhesive pad and at an edge thereof in a position that is expected to stay dry during a leakage; and a material coupled to the housing and configured to change colors when the medicament has leaked from the delivery device.

* * * * *